United States Patent [19]
Burrows et al.

[11] 4,000,012
[45] Dec. 28, 1976

[54] ANTICORROSIVE COATING OF STEEL

[75] Inventors: John Burrows, Congleton; James Roger Hargreaves, Sale; Peter Miles, Stockport, all of England

[73] Assignee: Ciba-Geigy Corporation, Ardsley, N.Y.

[22] Filed: Sept. 27, 1974

[21] Appl. No.: 509,875

[30] Foreign Application Priority Data

Oct. 6, 1973 United Kingdom ............ 46794/73

[52] U.S. Cl. .................. 148/6.15 R; 148/6.15 Z; 106/14; 252/389 A
[51] Int. Cl.² ........................................ C23F 7/10
[58] Field of Search ............... 148/6.15 R, 6.15 Z; 106/14; 21/2.5 A, 2.7 A; 252/389 A; 260/502.5

[56] References Cited

UNITED STATES PATENTS

| | | | |
|---|---|---|---|
| 3,200,004 | 8/1965 | Herbst et al. | 148/6.15 Z |
| 3,202,534 | 8/1965 | Duch et al. | 148/6.15 Z |
| 3,483,133 | 12/1969 | Hatch et al. | 106/14 |
| 3,634,146 | 1/1972 | Wystrach et al. | 148/6.15 R |

FOREIGN PATENTS OR APPLICATIONS

| | | |
|---|---|---|
| 1,570,819 | 6/1969 | France |
| 2,231,206 | 12/1972 | Germany |
| 1,230,121 | 1/1967 | United Kingdom ............ 260/502.5 |

OTHER PUBLICATIONS

B265,369, Jan. 1975, Harris et al., 106/14.

*Primary Examiner*—Ralph S. Kendall
*Assistant Examiner*—Charles R. Wolfe, Jr.
*Attorney, Agent, or Firm*—Charles W. Vanecek

[57] ABSTRACT

The corrosion protecting action of iron phosphate or zinc phosphate coatings on mild steel is markedly raised by treating with solutions of α-aminophosphonic or -phosphonous acids or their water soluble salts. Compounds having more than one amino and more than one phosphonic or phosphonous acid groups are also suitable. Paint films on metal surfaces pretreated in this manner show a considerably better adhesion than on untreated surfaces.

10 Claims, No Drawings

ANTICORROSIVE COATING OF STEEL

The present invention relates to the treatment of steel to improve the corrosion resistance.

Chromates are widely used to improve the corrosion resistance and reduce paint film blistering on phosphated mild steel. However large volumes of rinse water contaminated with hexavalent chromium ions are generated by the process and since chromate ions are toxic and pollute any steam or river into which water containing them is discharged, they are ecologically undesirable.

Surprisingly we have found that certain α-aminophosphonic acids and α-aminophosphonous acids can be used instead of the chromates and do not present the environmental disadvantages of the chromates.

According to the present invention there is provided a method of treating phosphated mild steel which comprises contacting the mild steel with a solution containing a compound of the formula:-

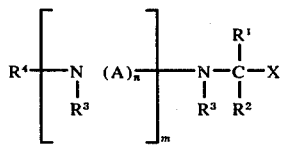

I.

in which $R^1$ is an aryl or substituted aryl grouping containing from 6 to 20 carbon atoms or an alkyl grouping containing up to 6 carbon atoms, $R^2$ is hydrogen or $R^1$ and $R^2$ together with the carbon atoms to which they are attached form a six-membered alicyclic ring, $R^3$ is hydrogen or an acyl grouping containing 2 or 3 carbon atoms and $R^4$ is a straight or branched alkyl grouping containing up to 20 carbon atoms, cycloalkyl containing 5 or 6 carbon atoms, an aralkyl or substituted aralkyl grouping or an aralkylene phosphonic acid grouping containing up to 20 carbon atoms, A is a saturated divalent alkylene radical containing up to 6 carbon atoms, X is a phosphonic or phosphonous acid grouping and m is 0, 1 or 2 and n is 0 or 1; or a water soluble salt thereof.

Preferably $R^2$ is hydrogen, X is a phosphonic acid grouping, m is 0 or 1 and A contains 1 or 2 carbon atoms.

When $R^1$ is an aryl or substituted aryl grouping it preferably contains from 6 to 15 carbon atoms and especially from 6 to 8 carbon atoms: when $R^4$ is an aralkyl or substituted aralkyl grouping or an aralkylene phosphonic acid grouping it preferably contains from 7 to 15 carbon atoms and especially 7 or 8 carbon atoms: when $R^4$ is an alkyl grouping it preferably contains 1 to 18 carbon atoms: when $R^4$ is a cycloalkyl grouping it is preferably cyclohexyl.

The α-aminophosphonic acids of formula I may be prepared by the method described in British Patent Application No. 34430/70. The α-aminophosphonous acids of formula I may be prepared by the method of W. M. Linfield, E. Jungermann and A. T. Guttmann, Journal of Organic Chemistry 26 (1961), 4088.

Examples of compounds of value in the present invention are:

| | List No. |
|---|---|
| 1. Phosphonic acids where X = $PO_3H_2$ | |
| a. m = O, $R^3$ = H | |
| α-Benzylamino benzyl phosphonic acid | 1 |
| α-n-Hexylamino heptyl phosphonic acid | 2 |
| α-n-Dodecylamino-m-nitrobenzyl phosphonic acid | 3 |
| α-n-Dodecylamino-o-chlorobenzyl phosphonic acid | 4 |
| α-n-Dodecylamino-p-methylbenzylphosphonic acid | 5 |
| α-Cyclohexylamino benzylphosphonic acid | 6 |
| α-Methylamino benzylphosphonic acid | 7 |
| α-n-Hexylamino benzylphosphonic acid | 8 |
| α-n-Octylaminobenzyl phosphonic acid | 9 |
| α-n-Dodecylamino benzylphosphonic acid | 10 |
| α-n-Octadecylamino benzyl phosphonic acid | 11 |
| b) m = O, $R^3$ = $CH_3CO$ | |
| N-Acetyl-α-cyclohexylamino benzyl phosphonic acid | 12 |
| 1-N-Acetylanilino cyclohexyl-1-phosphonic acid | 13 |
| 1-N-Acetyl-α-n-dodecylaminobenzyl phosphonic acid | 14 |
| c) m = O, $R^3$ = $CH_3CH_2CO$ | |
| N-Propionyl-α-cyclohexylamino benzyl phosphonic acid | 15 |
| d) m = 1, n = O, $R^3$ = H | |
| N,N'-hydrazino-α,α'-dibenzylphosphonic acid | 16 |
| e) m = 1, n = 1, $R^3$ = H | |
| N,N'-ethylene bis(iminobenzylidene)diphosphonic acid | 17 |
| N,N'-hexamethylene bis(iminobenzylidene)diphosphonic acid | 18 |
| f) m = 2 n = 1, $R^3$ = H | |
| N,N'-diethyleneamino bis(iminobenzylidene)diphosphonic acid | 19 |
| The α-amino phosphonic acids (e) and (f) may be prepared by the method of O. Forest & G. Thomas, Bull Soc.Chem. France 1968 (8) pg. 3441 | |
| 2. Phosphonous acids where X = $PO_2H_2$ | |
| m = O, $R^3$ = H | |
| α-n-Hexylamino benzyl phosphonous acid | 20 |
| α-n-Dodecylamino benzyl phosphonous acid | 21 |
| α-Cyclohexylamino benzyl phosphonous acid | 22 |
| Particularly preferred compounds are: | |
| α-Cyclohexylamino benzyl phosphonic acid | |
| α-Methylamino benzyl phosphonic acid | |
| α-n-Hexylamino benzyl phosphonic acid | |
| α-n-Octylamino benzyl phosphonic acid | |
| α-n-Dodecylamino benzyl phosphonic acid | |
| α-n-Octadecylamino benzyl phosphonic acid | |

The compound of formula I may be applied in the free acid, partial salt or salt form and when applied in the form of a water-soluble salt, the salt may be for instance, the sodium, potassium, ammonium or triethanolamine salt.

The phosphated mild steel may be treated with the compound of formula I or a water-soluble salt thereof by any suitable method of contacting a metal surface with a solution of the compound of formula I, for instance by immersion of the metal in the solution or painting or spraying onto the metal surface.

The compounds of formula I have been found to seal the phosphate coating on phosphated mild steel.

The present invention also provides new phosphated mild steel or zinc phosphated mild steel which has been treated with a compound of formula I.

The following Examples further illustrate the present invention.

EXAMPLES 1 to 12

Painted panels of zinc phosphate coated mild steel in Examples 1 to 8 and ferric phosphate coated mild steel in Examples 9 to 12 were prepared in the following manner.
1. Excess oil was wiped from a 3 inch by 2 inch, 20 S.W.G. "fully finished" test panel with absorbent tissue.

The panel was then successively:
2. Degreased in an acetone bath for approximately 5 minutes.
3. Air dried
4. Immersed in the following alkali cleaning bath:

| | | |
|---|---|---|
| Sodium hydroxide | 37.5 | grams per liter |
| Sodium carbonate | 25.0 | grams per liter |
| Trisodium phosphate (12H$_2$O) | 6.2 | grams per liter |
| Teepol (commercial detergent supplied by Shell Chemical UK,Ltd.) | 1.5 | grams per liter |
| at 80–90° C for approximately 5 minutes. | | |

5. Water rinsed for at least 30 seconds. A steady flow of tap water through the rinse bath was maintained to ensure that the phosphating bath did not become contaminated with alkali.
6. Phosphated in a "Bonderite 75" (commercial product supplied by Parcolene Co. Ltd.) bath for 5 minutes at 70° C to produce a zinc phosphated mild steel or for 2 minutes at 70° C in a "Bonderite 1000" (commercial product supplied by Parcolene Co. Ltd.) bath to produce a ferric phosphated mild steel. The baths were prepared according to the supplier's recommendations.
7. Rinsed for 30 seconds.
8. Immersed in a 1% weight/volume solution of the solubilised test compound for 1 minute at 70° C. Sufficient alkali is added to just solubilise the test compound to a pH of 3 to 10.
9. Rinsed for 15 to 30 seconds
10. Oven dried
11. The panel was then painted by dipping into a bath of "Synthetic Stoving Cream Enamel" Ref. RD 33321 supplied by A Holden and Son. The panel was removed, allowed to drain and stoved in an oven at 140° C for 20 minutes. Before using the paint, blank panels were painted and the film thickness measured using an Elcometer film thickness gauge. A film thickness of 1.25 thousandths of an inch (± 0.25) was obtained by adjusting the viscosity of the paint with a 2:1 mixture of 2-ethoxy ethanol:n-butanol.

Two tests were then carried out on the panels 1) Salt Spray test and 2) Exposure in an Environmental Test Cabinet. This simple vapour cabinet consists of a plywood box with an open top and ventilation slots on both sides at the base. A low wattage heating cable is mounted under a galvanised metal water pan inside this plywood box. The coated test panels are placed face down on top of the box so that the test surface is subjected to a highly humid atmosphere. The electrical input to the heater is adjusted by means of a variable transformer or rheostat. A thermometer located through a "blank" test panel into the vapour approximately 1 inch below the test surface indicates the vapour temperature. The reverse side of the test panel is exposed to normal room temperature so that the test surface is at a lower temperature than the vapour. Thus water vapour is continually condensed on the test surface during exposure.

Operation of the equipment is extremely simple requiring only an initial adjustment of the electrical input to maintain the required water vapour temperature. The water level in the water pan is maintained at a constant level by using a ballcock device to a mains water supply.

1. SALT SPRAY TEST

After preparation the panels were allowed to stand for 24 hours. Diagonals were then scored across the panels so that the paint film was broken. The panels were then subjected to continuous salt spray test according to ASTM B117 for 114 hours.

ASSESSMENT OF RESULT a. Corrosion

The panels were examined for corrosion and ranked according to the following scale:
A: Excellent — no corrosion in scored diagonals
B: Good — corrosion only in scored diagonals
C: Moderate — slight corrosion on paint surface
D: Fair — some corrosion on paint surface
E: Poor — severe corrosion on paint surface + indicates better than average within a category − indicates below average within a category b. Paint film adhesion

After the salt spray test the panel was washed and dried with a tea towel. The paint film adhesion was then estimated by firmly applying a strip of 1 inch wide "Sellotape" along one of the diagonals and then stripping it off.

The percentage of surface area of paint film remaining where the "Sellotape" had been applied was used as a criterion of paint film adhesion.

The results are given in Table I in which the tests in Examples 1 to 8 were on zinc phosphate coated mild steel and in Example 9 to 12 on ferric phosphate coated mild steel.

TABLE I

| Ex. | Compound | List No. | Corrosion Resistance | Adhesion |
|---|---|---|---|---|
| 1. | 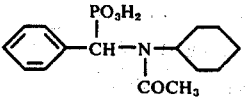 | 12 | C | 97 |
| 2. | 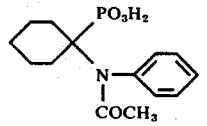 | 13 | C | 95 |
| 3. | 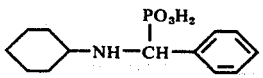 | 6 | B | 99 |
| 4. | 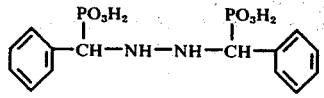 | 16 | B+ | 100 |
| 5. | 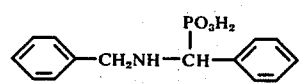 | 1 | C | 97 |
| 6. | 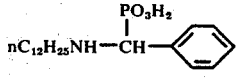 | 10 | B− | 97 |
| 7. | 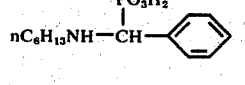 | 8 | B− | 90 |
| 8. | 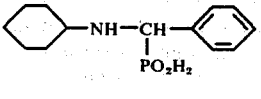 | 22 | B | 90 |
| 9. | 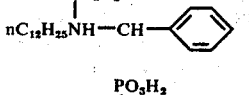 | 10 | B+ | 99 |
| 10. | 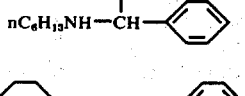 | 8 | B+ | 95 |
| 11. | 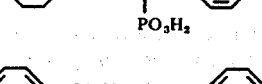 | 6 | B+ | 70 |
| 12. | 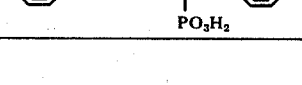 | 1 | B+ | 90 |

EXAMPLES 13 to 19

Test panels of zinc phosphate coated mild steel in Examples 13 to 16 and ferric phosphate coated mild steel in Examples 17 to 19 were prepared by the method described in Examples 1 to 12 except that a 0.25% weight/volume solution of the test compound was used to treat the phosphated panels. The panels were then painted as described but no diagonals were scored into the paint surface. After allowing 24 hours for conditioning the panels were exposed to continuously condensing water vapour at 48° C in an environmental test cabinet. After 16 days the panels were removed and examined for blistering of the paint film. The results are given in Table II.

TABLE II

| Ex. | Compound | List No. | Remarks |
|---|---|---|---|
| 13 | 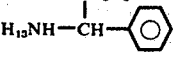 | 8 | Side edges and top of test panel covered in v. small blisters 85% surface free from blistering |
| 14 | 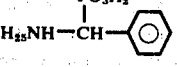 | 10 | Small blisters at top of panel 90% of surface blister free |
| 15 | 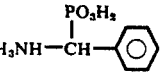 | 7 | Small blisters at top of panel 90% of surface blister free |

TABLE II-continued

| Ex. | Compound | List No. | Remarks |
|---|---|---|---|
| 16 | ⌬—NH—CH(PO₃H₂)—⌬ | 6 | Small blisters at top and edges of panel. 65% of surface blister free |
| 17 | nC₆H₁₃NH—CH(PO₃H₂)—⌬ | 8 | Blisters near top and edges of panel. 95% of surface blister free |
| 18 | nC₈H₁₇NH—CH(PO₃H₂)—⌬ | 9 | Blisters near top of panel. 98% of surface blister free |
| 19 | ⌬—NH—CH(PO₃H₂)—⌬ | 6 | Blisters near top of panel. 90% of surface blister free |

COMPARATIVE EXAMPLES A, B AND C.

In comparative Examples A and C a painted panel of zinc phosphate coated mild steel was prepared as in Examples 1 to 8 but using Parcolene 60 (a commercially available chromate solution for sealing phosphated steel) instead of the 1% weight/volume solution of the compound of formula I in Example A and no sealant in Example C. In Comparative Example B a painted panel of ferric phosphate coated mild steel was prepared as in Examples 9 to 12 but using Parcolene 60 as sealant instead of the solution of the compound of formula I.

The results after the salt spray test of corrosion resistance paint film adhesion are given in Table III.

TABLE III

| Comparative Example | Corrosion Resistance | % Adhesion |
|---|---|---|
| A | B+ | 100 |
| B | B | 100 |
| C | C | 80 |

These results show that the compounds of formula I compare well with Parcolene 60 and that mild steel panels have better corrosion resistance and paint adhesion properties when sealed with compounds of formula I than when no sealant is used.

COMPARATIVE EXAMPLES D AND E

In Comparative Example D, a painted panel of zinc phosphate coated mild steel was prepared as described in Examples 13 to 16 but using Parcolene 60 as sealant instead of the solution of the compound of formula I and in Comparative Example E a painted panel of ferric phosphate coated mild steel was prepared as described in Examples 17 to 19 but using Parcolene 60 as sealant instead of the solution of the compound of formula I.

The panels were then painted as described but no diagonals were scored into the paint surface. After allowing 24 hours for ageing the panels were exposed to continuously condensing water vapour at 48° C in an environmental test cabinet.

After 16 days the panels were removed and examined for blistering of the paint film.

The results are given in Table IV.

TABLE IV

| D | Parcolene 60 sealed zinc phosphate | Blisters near top and edges of panel 85% of surface blister free |
|---|---|---|
| E | Parcolene 60 sealed iron phosphate | Large blisters in centre of panel 70% of surface blister free |

We claim:
1. A method of treating phosphated mild steel, said method consisting essentially of
   a. contacting the mild steel with an aqueous solution of a compound of the formula:

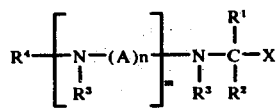

in which $R^1$ is an aryl or substituted aryl grouping containing from 6 to 20 carbon atoms or an alkyl grouping containing up to 6 carbon atoms, $R^2$ is hydrogen or $R^1$ and $R^2$ together with the carbon atoms to which they are attached form a six-membered alicyclic ring, $R^3$ is hydrogen or an acyl grouping containing 2 or 3 carbon atoms and $R^4$ is a straight or branched alkyl grouping containing up to 20 carbon atoms, cycloalkyl containing 5 or 6 carbon atoms, or aralkyl or substituted aralkyl grouping or an aralkylene phosphonic acid grouping containing up to 20 carbon atoms, A is a saturated divalent alkylene radical containing up to 6 carbon atoms, X is a phosphonic or phosphonous acid grouping and m is 0, 1 or 2 and n is 0 or 1; or a water-soluble salt thereof, to form a sealing coating on the steel, and
   b. drying the coated steel.
2. A method according to claim 1 in which the grouping A contains 1 or 2 carbon atoms.
3. A method according to claim 1 in which $R^1$ is an aryl or substituted aryl grouping containing from 6 to 8 carbon atoms.
4. A method according to claim 1 in which $R^4$ is an aralkyl or substituted aralkyl grouping or an aralkylene phosphonic acid grouping containing 7 or 8 carbon atoms.
5. A method according to claim 1 in which $R^4$ is an alkyl grouping containing from 1 to 18 carbon atoms.
6. A method according to claim 1 in which $R^4$ is a cyclohexyl grouping.
7. A method according to claim 1 in which the metal is immersed in a solution of a compound of formula I.
8. A method according to claim 1 in which a solution of a compound of formula I is painted or sprayed onto the metal surface.
9. Phosphated mild steel treated by the method of claim 1
10. A method according to claim 1 in which the coated and dried steel is painted.

* * * * *